(12) United States Patent
Scampoli

(10) Patent No.: US 10,471,228 B2
(45) Date of Patent: Nov. 12, 2019

(54) FLEXIBLE LOW DEADSPACE RESPIRATORY NOSEPIECE FOR GAS SAMPLING CANNULAE AND METHOD OF MANUFAC

(71) Applicant: KONINKLIJKE PHILIPS N.V., Eindhoven (NL)

(72) Inventor: David Scampoli, South Glastonbury, CT (US)

(73) Assignee: Koninklijke Philips N.V., Eindhoven (NL)

( * ) Notice: Subject to any disclaimer, the term of this patent is extended or adjusted under 35 U.S.C. 154(b) by 500 days.

(21) Appl. No.: 15/118,644

(22) PCT Filed: Feb. 12, 2015

(86) PCT No.: PCT/IB2015/051045
§ 371 (c)(1),
(2) Date: Aug. 12, 2016

(87) PCT Pub. No.: WO2015/121815
PCT Pub. Date: Aug. 20, 2015

(65) Prior Publication Data
US 2017/0049986 A1  Feb. 23, 2017

Related U.S. Application Data

(60) Provisional application No. 61/938,729, filed on Feb. 12, 2014.

(51) Int. Cl.
*A61M 16/08* (2006.01)
*A61M 16/06* (2006.01)
(Continued)

(52) U.S. Cl.
CPC ...... *A61M 16/085* (2014.02); *A61M 16/0672* (2014.02); *A61M 16/0816* (2013.01);
(Continued)

(58) Field of Classification Search
CPC .......... A61M 16/0461; A61M 16/0666; A61M 16/0672; A61M 16/0816; A61M 16/0841;
(Continued)

(56) References Cited

U.S. PATENT DOCUMENTS

| 4,989,599 | A |   | 2/1991 | Carter |
| 5,740,799 | A | * | 4/1998 | Nielsen ............. A61M 16/0666 128/207.18 |

(Continued)

FOREIGN PATENT DOCUMENTS

| CN | 2231113 Y | 7/1996 |
| DE | 2845346 A1 | 4/1980 |

(Continued)

*Primary Examiner* — Joseph D. Boecker

(57) ABSTRACT

A respiratory nosepiece (10) and method of manufacturing the respiratory nosepiece, the respiratory nosepiece including a first nasal prong (110) with a first channel (112) extending there through, and a first side port (130) connectable to tubes (192, 194) having different first and second diameters. The first side port has a second channel (131) extending there through and in communication with the first channel. The second channel includes a first section (134) having the first diameter, a second section (136) having the second diameter, a first step (135) between the first and second sections, and a second step (137) between the second section and an end (133) of the second channel. The first and second channels are formed during injection molding by pins (412, 422, 431, 441) having flat pin-on-pin geometry to reduce resin flash within the channels.

13 Claims, 4 Drawing Sheets

(51) Int. Cl.
   *B29C 45/36* (2006.01)
   *B29C 45/26* (2006.01)
   *B29L 31/00* (2006.01)

(52) U.S. Cl.
   CPC ............ *B29C 45/261* (2013.01); *B29C 45/36* (2013.01); *A61M 2202/0208* (2013.01); *A61M 2207/00* (2013.01); *A61M 2207/10* (2013.01); *A61M 2210/0625* (2013.01); *A61M 2230/432* (2013.01); *B29C 2045/366* (2013.01); *B29L 2031/753* (2013.01)

(58) Field of Classification Search
   CPC ............ A61M 16/085; A61M 2207/00; B29C 45/261; B29C 45/36; B29C 2045/366; B29L 2031/753
   See application file for complete search history.

(56) References Cited

U.S. PATENT DOCUMENTS

| | | | |
|---|---|---|---|
| 7,905,232 B2 | 3/2011 | Olsen et al. | |
| 8,146,591 B2 | 4/2012 | Niklewski et al. | |
| 8,631,799 B2 | 1/2014 | Davenport et al. | |
| 9,227,034 B2 | 1/2016 | Kapust et al. | |
| 9,358,358 B2 | 6/2016 | Wondka et al. | |
| 2005/0028821 A1* | 2/2005 | Wood | A61M 16/0666 128/207.18 |
| 2005/0252515 A1* | 11/2005 | Wood | A61M 16/0666 128/207.18 |
| 2006/0042638 A1 | 3/2006 | Niklewski et al. | |
| 2006/0130840 A1* | 6/2006 | Porat | A61M 16/0666 128/206.11 |
| 2008/0105318 A1 | 5/2008 | Leone | |
| 2010/0094366 A1 | 4/2010 | McCarthy | |
| 2010/0252037 A1 | 10/2010 | Wondka et al. | |
| 2010/0252044 A1 | 10/2010 | Duquette et al. | |
| 2014/0005565 A1* | 1/2014 | Derrick | A61B 5/097 600/532 |
| 2014/0158127 A1* | 6/2014 | Boucher | A61M 16/0683 128/203.22 |
| 2016/0175548 A1* | 6/2016 | Spence | A61M 16/16 128/203.22 |

FOREIGN PATENT DOCUMENTS

| | | | | |
|---|---|---|---|---|
| JP | H05505119 | | 8/1993 | |
| JP | 3157855 A | | 10/1993 | |
| JP | 2007229207 A | * | 9/2007 | ........ A61M 16/0672 |

* cited by examiner

FLEXIBLE LOW DEADSPACE RESPIRATORY NOSEPIECE FOR GAS SAMPLING CANNULAE AND METHOD OF MANUFAC

This application is a national stage application under 35 U.S.C. § 371 of International Application No. PCT/IB2015/051045 filed on Feb. 12, 2015 and published in the English language on Aug. 20, 2015 as International Publication No. WO 2015/121815 A1, which claims priority to U.S. Application No. 61/938,729 filed on Feb. 12, 2014, the entire disclosures of which are incorporated herein by reference.

TECHNICAL FIELD

The present invention is directed generally to respiratory nosepieces for gas sampling. More particularly, various inventive apparatuses and assembly methods disclosed herein relate to injection-molded respiratory nosepieces having low deadspace (low internal volume) and which are configured to maintain gas signal fidelity of a respiratory gas sample.

BACKGROUND

Existing respiratory nosepieces for gas sampling are typically made by dipping a wire frame into plastisol (a suspension of polyvinyl chloride (PVC) particles). The dipped wireframe is cured by heating, and the cured respiratory nosepiece is then hand-stripped off the wire frame. Such dipping processes are time consuming and expensive, but are however considered necessary to manufacture respiratory nosepieces having the low deadspace (low internal volume) required for gas sampling.

Conventional injection molding techniques generally are not used to manufacture respiratory nosepieces for gas sampling, because the small mold pin dimensions necessary to realize small diameter channels (low internal volume) typically result in resin flash that forms occlusions within the channels. The occlusions create turbulence within the sample gas flow, degrading gas sample signal fidelity.

It would be desirable to provide a low-cost respiratory nosepiece having low internal volume, and an efficient method of manufacturing a respiratory nosepiece that avoids formation of occlusions and maintains gas sample signal fidelity.

SUMMARY

The present disclosure is directed to respiratory nosepieces for gas sampling and methods of manufacturing respiratory nosepieces for gas sampling.

Generally, in one aspect, a respiratory nosepiece includes a first nasal prong configured to be insertable into a nostril of a patient, a first channel extending through the first nasal prong along a first direction; and a first side port connectable to tubes having different first and second diameters, the first side port including a second channel extending along a second direction orthogonal with respect to the first direction, the second channel having a first end configured to insertably receive the tubes and having a second end in communication with the first channel, the second channel comprising a first section at the first end having the first diameter, a second section having the second diameter, a first step between the first and second sections, and a second step between the second section and the second end of the second channel, the first step configured to prevent insertion of first tubes having the first diameter into the second section and the second step configured to prevent insertion of second tubes having the second diameter further into the second channel.

In one or more embodiments, the respiratory nosepiece further includes a second nasal prong configured to be insertable into another nostril of the patient, a third channel extending through the second nasal prong along the first direction; and a second side port connectable to the tubes, the second side port including a fourth channel extending along the second direction, the fourth channel having a first end configured to insertably receive the tubes and a second end in communication with the third channel, the fourth channel comprising a third section at the first end having the first diameter, a fourth section having the second diameter, a third step between the third and fourth sections, and a fourth step between the fourth section and the second end of the fourth channel, the third step configured to prevent insertion of the first tubes into the third section and the fourth step configured to prevent insertion of the second tubes further into the fourth channel.

In one or more embodiments, the respiratory nosepiece further includes a bridge section extending between the first and second side ports and configured to support the nosepiece against the patient.

In one or more embodiments, the second channel further includes an additional section having a third diameter smaller than the second diameter, the additional section extending between the second step and the second end of the second channel.

In one or more embodiments, an inner diameter of the first tube is substantially the same as the second diameter.

In one or more embodiments, the second end of the second channel has a spherical shape configured to smoothly redirect flow of gas between the first and second channels.

In one or more embodiments, the nosepiece is made of polyvinyl chloride, thermoplastic elastomer, silicone, ethylene propylene diene monomer, or urethane having a sufficiently low durometer to be flexible.

In one or more embodiments, a top surface of the bridge section is curved so that a height of the bridge section along the first direction is reduced near a center point between the first and second nasal prongs.

In one or more embodiments, side surfaces of the bridge section adjacent the top surface are curved so that a width between the side surfaces of the bridge section is reduced near the center point between the first and second nasal prongs.

In one or more embodiments, the respiratory nosepiece may further include a fifth channel in the bridge section, the fifth channel having a first end in communication with the second end of the second channel and having a second end; and an oral sampling port including a sixth channel extending along the first direction, the sixth channel having a first end in communication with the second end of the fifth channel and having a second end configured to be adjacent to a mouth of the patient.

In one or more embodiments, the oral sampling port is beveled toward the mouth of the patient at the second end of the sixth channel In another aspect, a method of manufacturing a respiratory nosepiece includes providing a first and second mold pieces, the first mold piece having a cavity in the shape of the nosepiece; placing the second mold piece against the first mold piece to enclose the cavity; inserting first and second pins through respective walls of the first and second mold pieces and into the cavity, so that a distal end of the first pin having a flat face is brought into direct contact with a flat sidewall portion of the second pin; and injecting a polymer into the cavity enclosed by the first and second mold pieces.

In one or more embodiments, the method may further include retracting the first and second pins from the first and second mold pieces; removing the second mold piece from the first mold piece; and removing the nosepiece from the first and second mold pieces.

In one or more embodiments, the polymer may be polyvinyl chloride, thermoplastic elastomer, silicone, ethylene propylene diene monomer, or urethane having a sufficiently low durometer to be flexible.

In one or more embodiments, the first and second pins are inserted through the first and second mold pieces in orthogonal directions with respect to each other.

In one or more embodiments, the second pin includes a first section having a first diameter, a second section having a second diameter, and a third section including the flat sidewall portion.

In one or more embodiments, a distal end of the second pin has a spherical shape.

In another aspect, a respiratory nosepiece includes first and second nasal prongs configured to be insertable into nostrils of a patient; a first side port having a first channel, the first channel having a first end configured to insertably receive tubes having different first and second diameters and a second end in communication with the first nasal prong; and a second side port having a second channel, the second channel having a first end configured to insertably receive the tubes and a second end in communication with the first nasal prong in communication with the second nasal prong, each of the first and second channels including a first section having the first diameter at the first end followed by a second section having the second diameter, wherein the first diameter is greater than the second diameter.

In one or more embodiments, each of the first and second channels further includes a third section following the second section, the third section having a third diameter smaller than the second diameter.

In one or more embodiments, the respiratory nosepiece further includes a bridge section extending between the first and second side ports and configured to support the nosepiece against the patient; a third channel in the bridge section, the third channel having a first end in communication with the second end of the first channel and having a second end; and an oral sampling port extending along a same direction as the first and second nasal prongs, the oral sampling port including a fourth channel having a first end in communication with the second end of the third channel and having a second end configured to be adjacent to a mouth of the patient.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

In the following detailed description, for purposes of explanation and not limitation, representative embodiments disclosing specific details are set forth in order to provide a thorough understanding of the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparatuses and methods may be omitted so as to not obscure the description of the representative embodiments. Such methods and apparatuses are clearly within the scope of the present teachings.

In view of the foregoing, various embodiments and implementations of the present invention are directed to a respiratory nosepiece for gas sampling and method of manufacturing a respiratory nosepiece for gas sampling.

Figure 1:
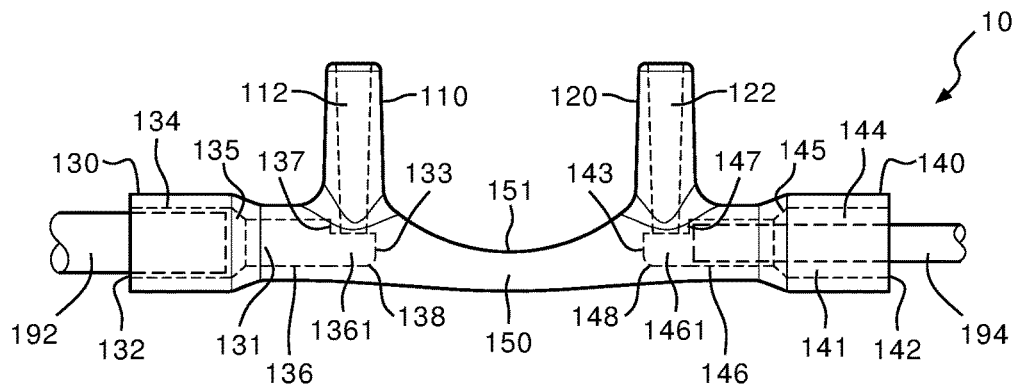
FIG. 1 illustrates a plan view of a respiratory nosepiece of an example embodiment including inserted tubing.

FIG. 1 illustrates a plan view of respiratory nosepiece 10 of an example embodiment including inserted tubes 192 and 194. Respiratory nosepiece 10 is made by injection molding, and may be a polymer material such as polyvinyl chloride, thermoplastic elastomer, silicone, ethylene propylene diene monomer, or urethane that has sufficiently low durometer to be flexible, such as in a range of about Shore A15 to Shore A90 for example.

Respiratory nosepiece 10 as shown in FIG. 1 is a nasal-only configuration, and includes first nasal prong 110 connected to first side port 130, second nasal prong 120 connected to second side port 140, and contoured bridge section 150 extending between first and second side ports 130 and 140. First and second nasal prongs 110 and 120 are insertable into the nostrils of a patient, and are relatively short for patient comfort. Prong-to-prong spacing between first and second nasal prongs 110 and 120 may be in a range of about 0.25 inches to 0.625 inches, suitable for a wide range of patient populations. First channel 112 depicted by dashed lines extends through first nasal prong 110 along a first (vertical) direction. First channel 112 has a substantially consistent diameter along the length of first nasal prong 110 that may be in a range of about 40-60 thousands of an inch. In an example embodiment, first channel 112 may taper slightly inward as it extends downward through first nasal prong 110.

First and second side ports 130 and 140 as shown in FIG. 1 are both connectable to tubes having different first and second diameters. First side port 130 includes a second channel 131 depicted by dashed lines that extends through it along a second (horizontal) direction orthogonal to the first (vertical) direction. Second channel 131 has a first end 132 that is configured to insertably receive the tubes, and a second end 133 in communication with first channel 112 of first nasal prong 110. Second channel 131 includes first section 134 at first end 132 that has the first diameter, second section 136 having the second diameter, first step 135 between first and second sections 134 and 136, and second step 137 between second section 136 and second end 133 of second channel 131. Second channel 131 further includes additional section 1361 having a third diameter smaller than the second diameter, additional section 1361 extending between second step 137 and second end 133 of second channel 131.

First step 135 is a transition having tapered diameter between first and second sections 134 and 136, and extends around the entire inner circumference of second channel 131. First step 135 functions as a hard stop that prevents insertion of first tubes, such as tube 192 which has the first diameter, into second section 136, so that second section 136 is not occluded by over-insertion of tube 192. Second step 137 is a transition between second section 136 and second end 133 of second channel 131. Second step 137 functions as a hard stop to prevent insertion of second tubes, such as tube 194 having the second diameter, further into second channel 131, so that additional section 1361 is not occluded by over-insertion of tube 194. Unlike first step 135, second step 137 is located only along an upper inner circumference of second channel 131 and consists of a wall portion which functions as a hard stop that abuts against an end face of an inserted tube such as tube 194 to prevent further insertion of the tube into second channel 131. Also, second end 133 of second channel 131 has a spherical shape at 138 to smoothly direct flow of gas between first and second channels 112 and 131 and minimize turbulence within the gas flow.

Third channel 122 shown in FIG. 1 depicted by dashed lines extends through second nasal prong 120 along the first (vertical) direction. Third channel 122 has a substantially consistent diameter along the length of second nasal prong 120 that may be in a range of about 40-60 thousands of an inch. Third channel 122 may taper slightly inward as it extends downward through second nasal prong 120.

Second side port 140 includes a fourth channel 141 depicted by dashed lines that extends through it along the second (horizontal) direction, orthogonal to the first (vertical) direction. Fourth channel 141 has a first end 142 that is configured to insertably receive the tubes, and a second end 143 in communication with third channel 122 of second nasal prong 120. Fourth channel 141 includes third section 144 at first end 142 that has the first diameter, fourth section 146 having the second diameter, third step 145 between third and fourth sections 144 and 146, and fourth step 147 between fourth section 146 and second end 143 of fourth channel 141. Fourth channel 141 further includes additional section 1461 having a third diameter smaller than the second diameter, additional section 1461 extending between fourth step 147 and second end 143 of fourth channel 141.

Third step 145 is a transition having tapered diameter between third and fourth sections 144 and 146, and extends around the entire inner circumference of fourth channel 141. Third step 145 functions as a hard stop that prevents insertion of first tubes, such as tube 192 which has the first diameter, into fourth section 146, so that fourth section 146 is not occluded by over-insertion of tube 192. Fourth step 147 is a transition between fourth section 146 and second end 143 of fourth channel 141. Fourth step 147 functions as a hard stop to prevent insertion of second tubes, such as tube 194 having the second diameter, further into fourth channel 141, so that additional section 1461 is not occluded by over-insertion of tube 194. Unlike third step 145, fourth step 147 is located only along an upper inner circumference of fourth channel 141 and consists of a wall portion which functions as a hard stop that abuts against an end face of an inserted tube such as tube 194 to prevent further insertion of the tube into fourth channel 141. Also, second end 143 of fourth channel 141 has a spherical shape at 148 to smoothly direct flow of gas between third and fourth channels 122 and 141 and minimize turbulence within the gas flow.

In an example embodiment, tube 192 connected to first side port 130 and inserted into first section 134 of second channel 131 as shown in FIG. 1 may be an oxygen delivery tube connected to an oxygen delivery system (not shown). Tube 192 may have an outer diameter of about 125 thousands of an inch, substantially corresponding to the first diameter of first section 134 of second channel 131 and third section 144 of fourth channel 141. In another example embodiment, tube 194 connected to second side port 140 and inserted through third section 144 and into fourth section 146 of fourth channel 141 as shown in FIG. 1 may be a carbon dioxide ($CO_2$) sampling tube connected to a respiratory gas monitoring device (not shown). Tube 194 may have an outer diameter of about 93 thousands of an inch, substantially corresponding to the second diameter of second section 136 of second channel 131 and fourth section 146 of fourth channel 141.

In example embodiments, tubes 192 may be bonded to first and third steps 135 and 145, and tubes 194 may be bonded to second and fourth steps 137 and 147 by adhesive or solvent bonding. In other example embodiments, tubes 192 and 194 may be attached to the inner walls of second and fourth channels 131 and 141 by barbed protrusions (not shown) extending from the outer walls of tubes 192 and 194.

Moreover, as should be readily understood, first and second side ports 130 and 140 as shown in FIG. 1 are both configured to insertably receive either tube 192 which may be an oxygen delivery tube, or tube 194 which may be a $CO_2$ gas sampling tube. In the example embodiment as shown in FIG. 1, by insertion of tube 192 into first side port 130 and insertion of tube 194 into second side port 140, a gas sampling cannulae including respiratory nosepiece 10 and tubes 192 and 194 may thus be provided by which respiratory $CO_2$ gas exhaled by the patient may be delivered via first side port 130 to a respiratory gas monitoring device (not shown) and by which oxygen may be delivered from an oxygen supply (not shown) to the patient via second side port 140. In a further embodiment, by insertion of tubes 192 into both first and second side ports 130 and 140, a gas sampling cannulae including respiratory nosepiece 10 and tubes 192 may thus be provided by which respiratory $CO_2$ gas exhaled by the patient may be delivered to a respiratory gas monitoring device (not shown) via both first and second side ports 130 and 140. Accordingly, by having first and second side ports 130 and 140 which may be characterized as universal side ports, respiratory nosepiece 10 configured as shown in FIG. 1 thus efficiently combines the functionality of two different types of respiratory nosepieces.

As described, respiratory nosepiece 10 may be made of sufficiently low durometer material to be flexible. When respiratory nosepiece 10 is attached to a patient with first and second nasal prongs 110 and 120 inserted into the nostrils, contoured bridge section 150 shown in FIG. 1 may be positioned under the nose to support respiratory nosepiece 10 against the nasal philtrum of the patient, and tubes 192 and 194 connected to either of first and second side ports 130 and 140 may be draped behind the ears of patient. In an example embodiment, a top surface 151 of contoured bridge section 150 may be curved so that a height of contoured bridge section 150 along the first (vertical) direction may be reduced near a center point between first and second nasal prongs 110 and 120. The reduction in cross-sectional height provides a contoured bridge section 150 that extends away from the nasal columella of the patient when respiratory nosepiece 10 is attached, avoiding uncomfortable chafing.

Figure 2:
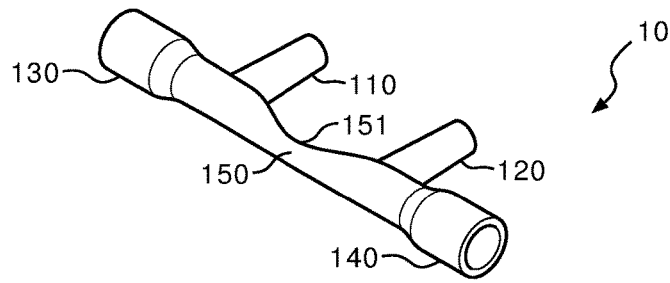
FIG. 2 illustrates a perspective view of a respiratory nosepiece of an example embodiment.

FIG. 2 illustrates a perspective view of respiratory nosepiece 10 of an example embodiment. First and second nasal prongs 110 and 120, first and second side ports 130 and 140, and contoured bridge section 150 including top surface 151 of respiratory nosepiece 10 are shown in FIG. 2.

Figure 3:
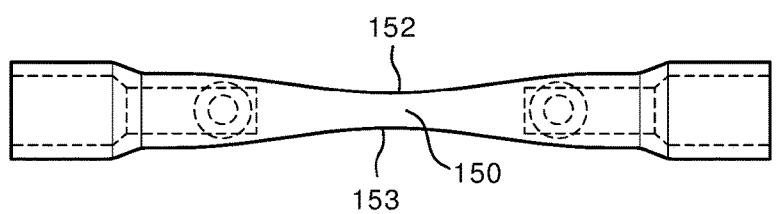
FIG. 3 illustrates a bottom plan view of a respiratory nosepiece of an example embodiment.

FIG. 3 illustrates a bottom plan view of respiratory nosepiece 10 of an example embodiment, from an underside of the view shown in FIG. 1. Contoured bridge section 150 as shown in FIG. 3 includes side surfaces (sidewalls) 152 and 153 that are adjacent top surface 151. Side surfaces 152 and 153 as shown may be curved inward so that a width between side surfaces 152 and 153 of contoured bridge section 150 may be reduced near a center point between first and second nasal prongs 110 and 120 (not shown). The reduction in width allows for greater flexibility at contoured bridge section 150, thus providing a more comfortable fit against the nasal philtrum of the patient.

Figure 4:
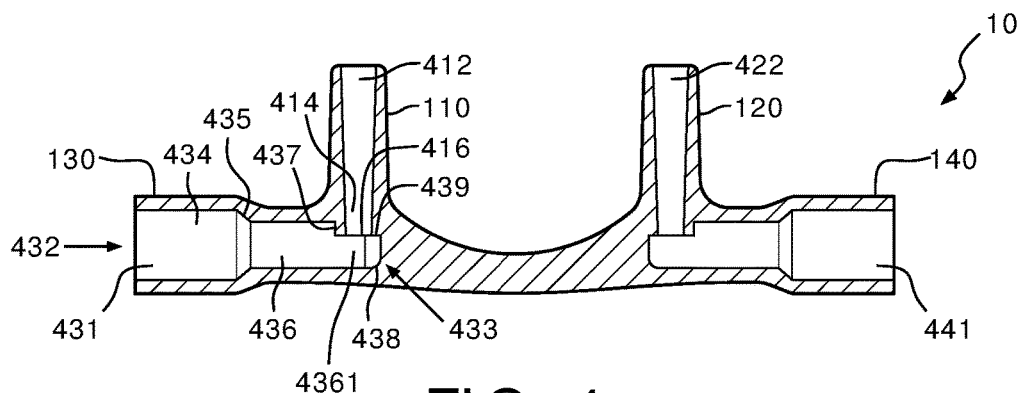
FIG. 4 illustrates a cross-sectional view of a respiratory nosepiece of an example embodiment, including pins.

FIG. 4 illustrates a cross-sectional view of respiratory nosepiece 10 of an example embodiment, including first and second pins 412 and 431. First and second pins 412 and 431 are inserted into a molding apparatus during an injection molding process as will be subsequently described with respect to FIGS. 5 and 6, to respectively form first channel 112 within first nasal prong 110 and second channel 131 within first side port 130. First and second pins 412 and 431 may be made of steel or aluminum, and are inserted into the molding apparatus prior to injection of molding material. FIG. 4 thus shows a cross-section of respiratory nosepiece 10 after injection of mold material, but before retraction of first and second pins 412 and 431, for purposes of explanation as follows.

First pin 412 as shown in FIG. 4 is substantially cylindrical, including distal end 414 that has a substantially flat face 416. First pin 412 has a substantially consistent diameter along its length, but may be slightly tapered toward distal end 414 so as to be more easily retractable after injection of the molding material. Second pin 431 includes first and second ends 432 and 433, first section 434 having the first diameter, second section 436 having the second diameter, and third section 4361 having a flat sidewall portion 439 aligned underneath and in direct contact with first pin 412 when first and second pins 412 and 431 are in the fully inserted position within the molding apparatus immediately prior to injection of the molding material. As can be appreciated in view of FIG. 7, first and second pins 412 and 431 are constructed so that flat face 416 at distal end 414 of first pin 412 is brought directly into contact with flat sidewall portion 439 of second pin 431 so that first pin 412 contacts flat sidewall portion 439 of second pin 431 substantially without any gaps or spaces there between, thus avoiding resin flash into first and second channels 112 and 131 of respiratory nosepiece 10 during injection molding. First and second pins 412 and 413 thus include respective opposing contact areas having flat pin-on-pin geometry. A smooth transition may thus be provided between first and second channels 112 and 131 of respiratory nosepiece 10 without turbulence of gas flow.

As further shown in FIG. 4, second pin 431 includes stepped portion 435 as a transition between first and second sections 434 and 436, stepped portion 435 forming first step 135 within second channel 131 of respiratory nosepiece 10. Second pin 431 further includes wall 437 as a transition between second section 436 and flat sidewall portion 439 of third section 4361. Wall 437 forms second step 137 within second channel 131. First and second sections 434 and 436 of second pin 431 are substantially cylindrical, while third section 4361 includes a substantially cylindrical bottom portion having flat sidewall portion 439 as a top surface. As further shown, second (distal) end 433 of second pin 431 has spherical shaped section 438 that correspondingly forms the spherical shape 138 at second end 133 within second channel 131, which helps to smoothly redirect gas flow between first and second channels 112 and 131 while minimizing turbulence.

Respiratory nosepiece 10 shown in FIG. 4 further includes third pin 422 within second nasal prong 120 that forms third channel 122 of respiratory nosepiece 10, and fourth pin 441 within second side port 140 that forms fourth channel 141. Third and fourth pins 422 and 441 are respectively substantially identical to first and second pins 412 and 431. Detailed description of third and fourth pins 422 and 441 is thus omitted.

Figure 5:
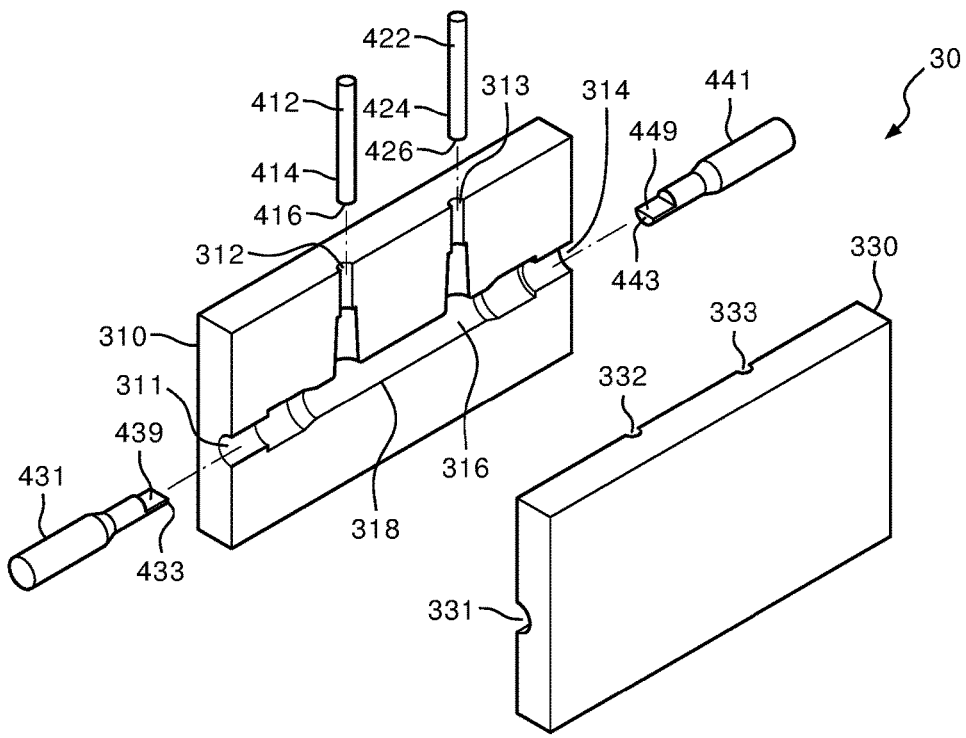
FIG. 5 illustrates a perspective view of a molding apparatus including first and second mold pieces and pins of an example embodiment.
Figures 6, 7:
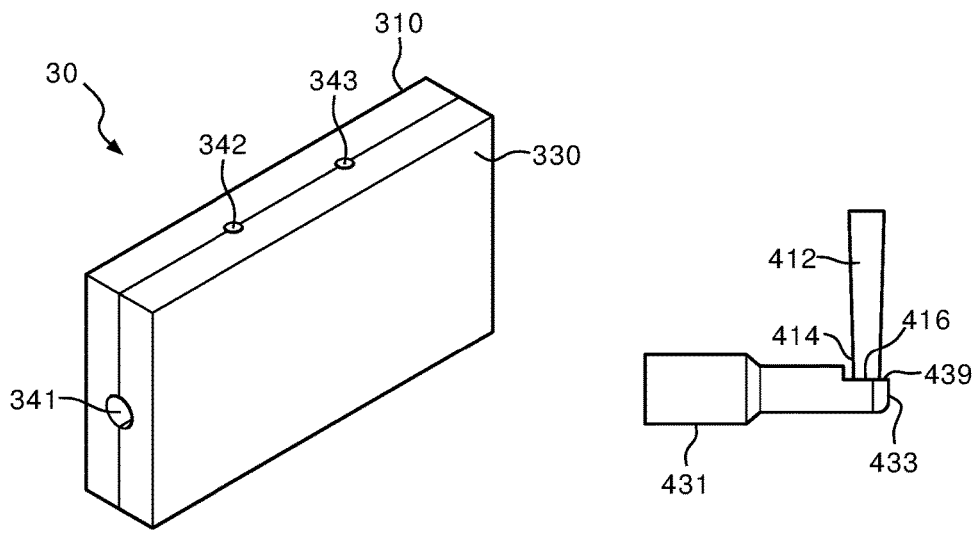
FIG. 6 illustrates a perspective view of a molding apparatus of an example embodiment with a first and second mold pieces closed together.
FIG. 7 illustrates a perspective view of pins of an example embodiment in contact with each other.

FIG. 5 illustrates a perspective view of molding apparatus 30 including first and second mold pieces 310 and 330, first pin 412, second pin 431, third pin 422 and fourth pin 441, of an example embodiment. Molding apparatus 30 is shown in FIG. 5 during an initial position with first and second mold pieces 310 and 330 apart from each other, and first through fourth pins 412, 422, 431 and 441 in retracted positions. FIG. 6 illustrates a perspective view of molding apparatus 30 of an example embodiment, with first and second mold pieces 310 and 330 closed together.

First mold piece 310 as shown in FIG. 5 includes cavity 316 which forms a first half of respiratory nosepiece 10. Second mold piece 330 includes an additional cavity (not shown) which forms a second half of respiratory nosepiece 10. In a molding process, first and second mold pieces 310 and 330 are brought together against each other, so that a complete nosepiece cavity is formed by cavity 316 and the additional cavity (not shown). Grooves 311, 312, 313 and 314 are formed in first mold piece 310, while corresponding mating grooves 331, 332, 333 and an additional groove (not shown) are formed in second mold piece 330. As shown in closed mold apparatus 30 of FIG. 6, the mating grooves of first and second mold pieces 310 and 330 form corresponding pin insertion holes 342, 341, 343 and a corresponding fourth pin insertion hole (not shown), into which first, second, third and fourth pins 412, 431, 422 and 441 are inserted through the walls of closed mold apparatus 30 and into the nosepiece cavity.

When the pins are fully inserted, flat face 416 at distal end 414 of first pin 412 shown in FIG. 5 will be in direct contact with flat sidewall portion 439 at second end 433 of second pin 431 substantially without any gap there between, as shown in FIG. 7. First and second pins 412 and 431 as inserted into mold apparatus 30 respectively form first and second channels 112 and 131 of respiratory nosepiece 10, first and second channels 112 and 131 being in communication with each other. Likewise, when the pins are fully inserted, flat face 426 at distal end 424 of third pin 422 shown in FIG. 5 will be in direct contact with flat sidewall portion 449 at second end 443 of fourth pin 441 substantially without any gap there between. Third and fourth pins 422 and 441 as inserted into mold apparatus 30 respectively form third and fourth channels 122 and 141 of respiratory nosepiece 10, third and fourth channels 122 and 141 being in communication with each other.

Additionally, an injection port (not shown) may be formed through first mold piece 310 to supply mold material at a location such as location 318 shown in FIG. 5. Positioning of the injection port to supply mold material to the nosepiece cavity at location 318 ensures that top surface 151 and/or side surfaces 152 and 153 of contoured bridge section 150 of respiratory nosepiece 10 as shown in FIGS. 1-3 will be substantially smooth without bumps, minimizing irritation when respiratory nosepiece 10 is attached to the patient.

FIG. 7 illustrates a perspective view of first and second pins 412 and 431 of an example embodiment as fully inserted into molding apparatus and in contact with each other. Distal end 414 of first pin 412 includes flat face 416 in direct contact with flat sidewall portion 439 at second end 433 of second pin 431 substantially without any gap there between, to minimize and avoid resin flash into respective first and second channels 112 and 131 of respiratory nosepiece 10.

Figure 8:
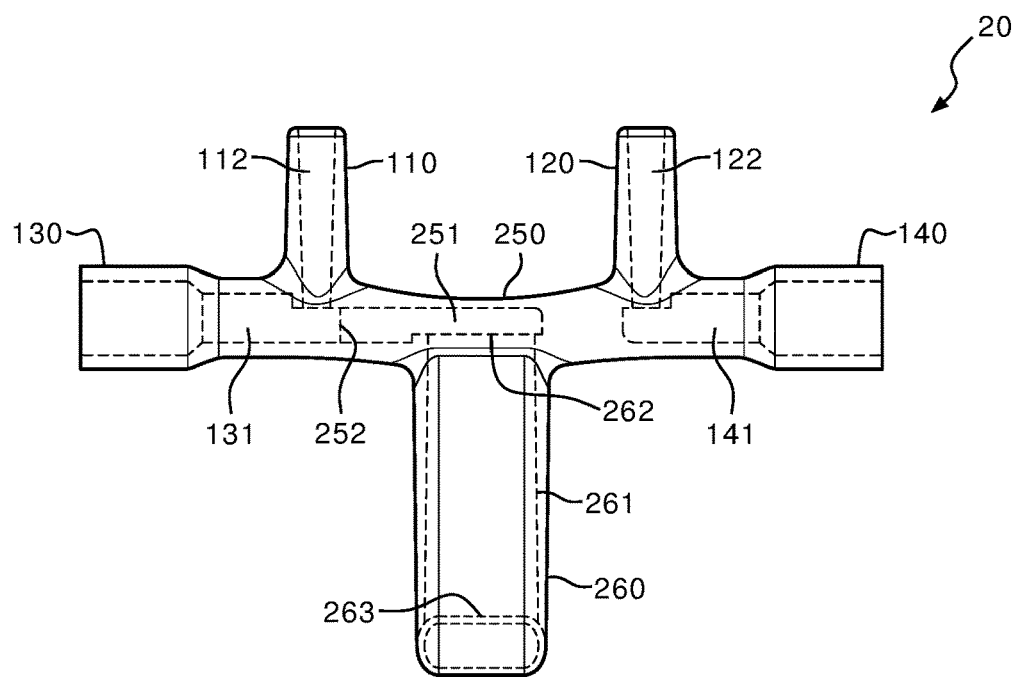
FIG. 8 illustrates a plan view of a respiratory nosepiece of an example embodiment including an oral sampling port.

FIG. 8 illustrates a perspective view of respiratory nosepiece 20 of an example embodiment, including an oral sampling port 260. Respiratory nosepiece 20 as shown in FIG. 8 includes first nasal prong 110, first channel 112, first side port 130, second channel 131, second nasal prong 120, third channel 122, second side port 140 and fourth channel 141 such as described with respect to FIG. 1, and for which detailed description with reference to FIG. 8 is omitted. First through fourth channels 112, 131, 122 and 141 as respectively extending through first nasal prong 110, first side port 130, second nasal prong 120 and second side port 140 are depicted by dashed lines.

Figure 10:
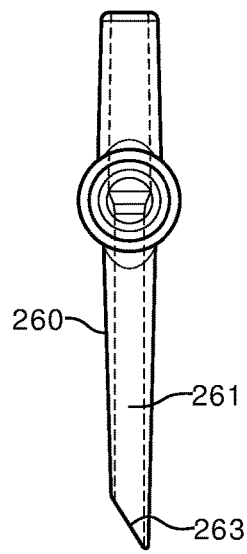
FIG. 10 illustrates a side plan view of an oral sampling port of an example embodiment.

Respiratory nosepiece 20 as shown in FIG. 8 further includes oral sampling port 260 and fifth channel 251 in bridge section 250. Fifth channel 251 includes first end 252 in communication with second channel 131 within first side port 130, and second end 253. Oral sampling port 260 includes sixth channel 261 which extends along the first (vertical) direction. Sixth channel 261 includes first end 262 in communication with second end 253 of fifth channel 251, and second end 263. Oral sampling port 260 is configured so that when respiratory nosepiece 20 is attached to a patient, second end 263 may be adjacent a mouth of the patient. As shown in FIG. 10, second end 263 of oral sampling port 260 may be beveled toward the mouth of the patient.

Respiratory nosepiece 20 as shown in FIG. 8 is designed for patients that are prone to mouth breathing in addition to or in place of nose breathing. In an example embodiment, first side port 130 of respiratory nosepiece 20 as shown in FIG. 8 may be connected to a respiratory gas monitoring device (not shown) via a $CO_2$ sampling tube such as tube 194 shown in FIG. 1 which has an outer diameter substantially corresponding to the second diameter. In other example embodiments, first side port 130 of respiratory nosepiece 20 as shown in FIG. 8 may be connected to an oxygen supply (not shown) via an oxygen delivery tube such as tube 192 shown in FIG. 1 which has an outer diameter substantially corresponding to the first diameter.

Figure 9:
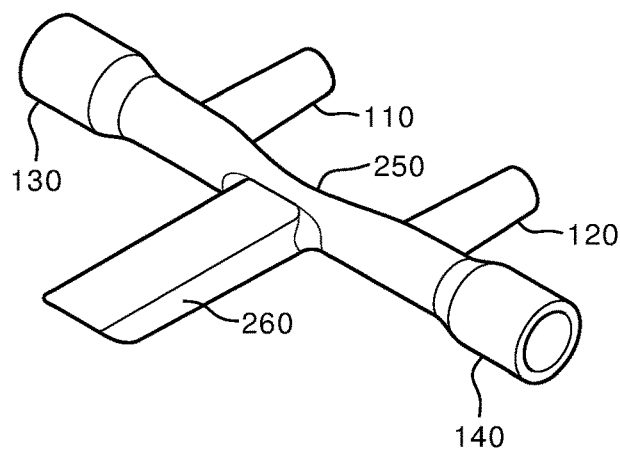
FIG. 9 illustrates a perspective view of a respiratory nosepiece including an oral sampling port of an example embodiment.

FIG. 9 illustrates a perspective view of respiratory nosepiece 20, including oral sampling port 260 of an example embodiment. First and second nasal prongs 110 and 120, first and second side ports 130 and 140, bridge section 250 and oral sampling port 260 of respiratory nosepiece 20 are shown in FIG. 9.

FIG. 10 illustrates a side plan view of oral sampling port 260 of respiratory nosepiece 20 of an example embodiment. As shown in FIG. 9, second end 263 of sixth channel 261 of oral sampling port 260 is beveled toward a mouth of the patient (not shown and which would be located to the left of the figure).

Figure 11:
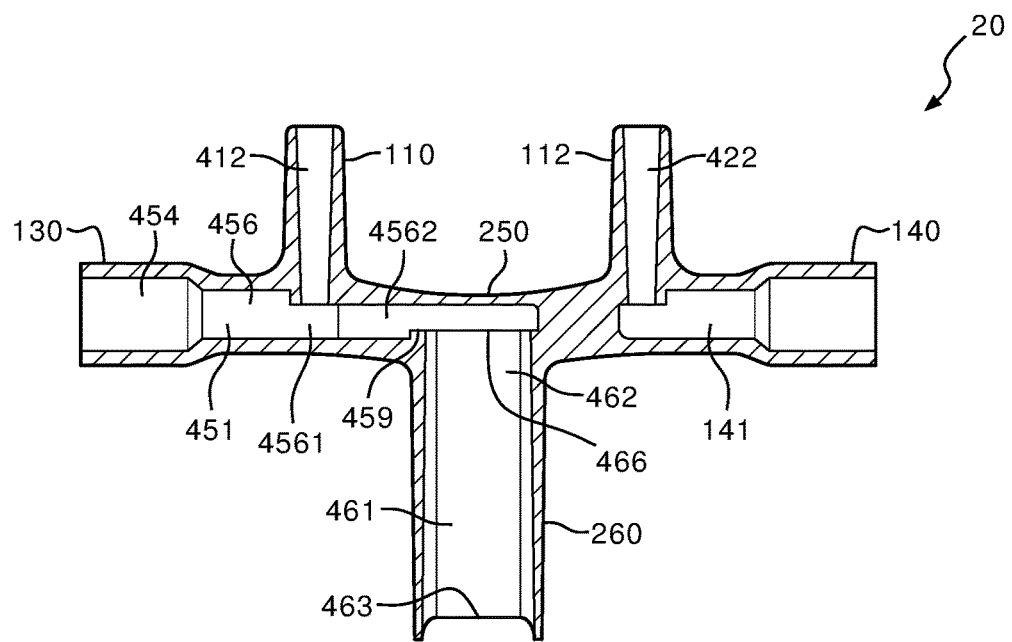
FIG. 11 illustrates a cross-sectional view of a respiratory nosepiece having an oral sampling port of an example embodiment, including pins.

FIG. 11 illustrates a cross-sectional view of respiratory nosepiece 20 of an example embodiment, including fifth and sixth pins 451 and 461. Fifth pin 451 is insertable into a molding apparatus such as shown in FIGS. 5 and 6 during an injection molding process to form second channel 131 and fifth channel 251 within bridge section 250 of respiratory nosepiece 20 shown in FIG. 8. Sixth pin 461 is insertable into the molding apparatus during the injection molding process to form sixth channel 261 within oral sampling port 260. Fifth pin 451 may be a pin similar in construction to second pin 431 described with respect to FIG. 4, including first, second and third sections 454, 456 and 4561 respectively corresponding to first, second and third sections 434, 436 and 4361 of second pin 431, and further including fourth section 4562 extending from third section 4561. Fifth pin 451 may include flat sidewall portion 459 at fourth section 4562. Sixth pin 461 may have a flat end face 466 at second (distal) end 462. When fully inserted into the corresponding molding apparatus, flat end face 466 of sixth pin 461 is brought into direct contact with flat sidewall portion 459 at fourth section 4562 of fifth pin 451 with no gaps there between, to minimize and avoid resin flash into fifth and sixth channels 251 and 261 of respiratory nosepiece 20.

As a variation, a multi-cavity tool may be provided including first and second mold pieces 310 and 330 having cavity 316 as shown in FIG. 5 for example repeated multiple times within an injection mold tool frame, with each cavity/core combination having its own set of pins. The overall mechanism of the injection mold tool would correspondingly actuate the pins for each cavity/core set.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 211.

The invention claimed is:

1. A respiratory nosepiece comprising:
   a first nasal prong configured to be insertable into a nostril of a patient, a first channel extending through the first nasal prong along a first direction; and
   a first side port connectable to tubes having different first and second diameters, the first side port including a second channel extending along a second direction orthogonal with respect to the first direction, the second channel having a first end configured to insertably receive the tubes and having a second end in communication with the first channel,
   the second channel comprising a first section at the first end having the first diameter, a second section having the second diameter, a first step between the first and second sections, and a second step between the second section and the second end of the second channel, the first step configured to prevent insertion of first tubes having the first diameter into the second section and the second step configured to prevent insertion of second tubes having the second diameter further into the second channel, and
   the second step consists of a wall portion located only along an upper inner circumference of the second channel.

2. The respiratory nosepiece of claim 1, further comprising:
   a second nasal prong configured to be insertable into another nostril of the patient, a third channel extending through the second nasal prong along the first direction; and
   a second side port connectable to the tubes, the second side port including a fourth channel extending along the second direction, the fourth channel having a first end configured to insertably receive the tubes and a second end in communication with the third channel, the fourth channel comprising a third section at the first end having the first diameter, a fourth section having the second diameter, a third step between the third and fourth sections, and a fourth step between the fourth section and the second end of the fourth channel, the third step configured to prevent insertion of the first tubes into the third section and the fourth step configured to prevent insertion of the second tubes further into the fourth channel.

3. The respiratory nosepiece of claim 2, further comprising a bridge section extending between the first and second side ports and configured to support the respiratory nosepiece against the patient.

4. The respiratory nosepiece of claim 1, wherein the second channel further comprises an additional section having a third diameter smaller than the second diameter, the additional section extending between the second step and the second end of the second channel.

5. The respiratory nosepiece of claim 4, wherein the first diameter is larger than the second diameter by an amount which corresponds to a wall thickness of the first tubes.

6. The respiratory nosepiece of claim 1, wherein the second end of the second channel has a spherical shape configured to smoothly redirect flow of gas between the first and second channels.

7. The respiratory nosepiece of claim 1, comprised of polyvinyl chloride, thermoplastic elastomer, silicone, ethylene propylene diene monomer, or urethane having a sufficiently low durometer to be flexible.

8. The respiratory nosepiece of claim 3, wherein a top surface of the bridge section is curved so that a height of the bridge section along the first direction is reduced near a center point between the first and second nasal prongs.

9. The respiratory nosepiece of claim 8, wherein side surfaces of the bridge section adjacent the top surface are curved so that a width between the side surfaces of the bridge section is reduced near the center point between the first and second nasal prongs.

10. The respiratory nosepiece of claim 3, further comprising:
 a fifth channel in the bridge section, the fifth channel having a first end in communication with the second end of the fourth channel and having a second end; and
 an oral sampling port including a sixth channel extending along the first direction, the sixth channel having a first end in communication with the second end of the fifth channel and having a second end configured to be adjacent to a mouth of the patient.

11. The respiratory nosepiece of claim 10, wherein the oral sampling port is beveled toward the mouth of the patient at the second end of the sixth channel.

12. A respiratory nosepiece comprising:
 first and second nasal prongs configured to be insertable into nostrils of a patient;
 a first side port having a first channel, the first channel having a first end configured to insertably receive tubes having different first and second diameters and a second end in communication with the first nasal prong; and
 a second side port having a second channel, the second channel having a first end configured to insertably receive the tubes and a second end in communication with the second nasal prong,
 each of the first and second channels comprising
  a first section having the first diameter at the first end followed by a second section having the second diameter, wherein the first diameter is greater than the second diameter,
  a third section following the second section, the third section having a third diameter smaller than the second diameter, and
  a step between the second and third sections, and consisting of a wall portion only located along an upper inner circumference of the second channel.

13. The respiratory nosepiece of claim 12, further comprising:
 a bridge section extending between the first and second side ports and configured to support the nosepiece against the patient;
 a third channel in the bridge section, the third channel having a first end in communication with the second end of the first channel and having a second end; and
 an oral sampling port extending along a same direction as the first and second nasal prongs, the oral sampling port including a fourth channel having a first end in communication with the second end of the third channel and having a second end configured to be adjacent to a mouth of the patient.

* * * * *